(12) United States Patent
Chowdhury

(10) Patent No.: US 10,076,495 B2
(45) Date of Patent: Sep. 18, 2018

(54) STRUCTURES FOR TRANSDERMAL DRUG DELIVERY

(75) Inventor: Dewan Fazlul Hoque Chowdhury, Leicestershire (GB)

(73) Assignee: Nemaura Pharma Limited, Leicestershire (GB)

(*) Notice: Subject to any disclaimer, the term of this patent is extended or adjusted under 35 U.S.C. 154(b) by 1028 days.

(21) Appl. No.: 13/816,170

(22) PCT Filed: Aug. 10, 2011

(86) PCT No.: PCT/GB2011/051512
§ 371 (c)(1),
(2), (4) Date: Feb. 8, 2013

(87) PCT Pub. No.: WO2012/020261
PCT Pub. Date: Feb. 16, 2012

(65) Prior Publication Data
US 2013/0144261 A1 Jun. 6, 2013

(30) Foreign Application Priority Data
Aug. 10, 2010 (GB) .................................. 1013405.4

(51) Int. Cl.
*A61M 35/00* (2006.01)
*A61K 9/14* (2006.01)
(Continued)

(52) U.S. Cl.
CPC .............. *A61K 9/14* (2013.01); *A61K 9/0021* (2013.01); *A61K 9/7023* (2013.01); *A61M 35/00* (2013.01);
(Continued)

(58) Field of Classification Search
CPC ...... A61M 37/0015; A61M 2037/0023; A61M 2037/0046; A61M 2037/0053; A61K 9/14; A61K 9/0021
(Continued)

(56) References Cited

U.S. PATENT DOCUMENTS 6,835,184 B1* 12/2004 Sage .................... A61B 17/205
604/20
8,764,712 B2* 7/2014 Melsheimer ......... A61K 9/0021
604/173
(Continued)

FOREIGN PATENT DOCUMENTS

DE          60010919     6/2005
JP          2003-530154  10/2003
(Continued)

OTHER PUBLICATIONS

International Search Report from the European Patent Office dated Jul. 7, 2010, for International Patent Application No. PCT/GB2011/051512, filed Aug. 10, 2011, Applicant, Nemaura Pharma Limited, (3 pages).
(Continued)

*Primary Examiner* — Laura Bouchelle
(74) *Attorney, Agent, or Firm* — McCracken & Gillen LLC

(57) ABSTRACT

A preparation for the transdermal delivery of a biologically active substance into the body of a patient comprises particles of a formulation comprising the active substance. The particles are irregular in size and shape and may be produced by a low cost manufacturing method such as grinding from a thin film. The particles are angular, i.e. they have sharp edges and corners that allow them to penetrate the outer layer of the skin when subjected to pressure from a roller or an array of blunt-tipped microstructures. Sucrose may be
(Continued)

Figure 1:
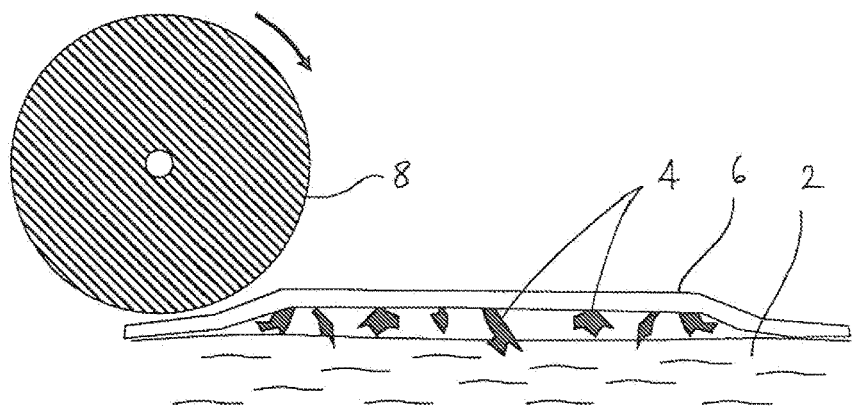

used as an excipient with the active substance to form suitably rigid and angular particles.

6 Claims, 2 Drawing Sheets

(51) Int. Cl.
*A61K 9/00* (2006.01)
*A61K 9/70* (2006.01)
*B32B 5/16* (2006.01)
*A61M 37/00* (2006.01)

(52) U.S. Cl.
CPC .......... *A61M 37/0015* (2013.01); *B32B 5/16* (2013.01); *A61M 2037/0007* (2013.01); *Y10T 428/2982* (2015.01)

(58) Field of Classification Search
USPC .................. 604/22, 46, 48, 57, 58, 289, 309
See application file for complete search history.

(56) References Cited

U.S. PATENT DOCUMENTS

2003/0134424 A1 7/2003 Canham et al.
2006/0177494 A1* 8/2006 Cormier ............... A61K 9/0021
424/449
2010/0042050 A1 2/2010 Chowdhury

FOREIGN PATENT DOCUMENTS

| | | |
|---|---|---|
| JP | 2005272398 | 10/2005 |
| JP | 2006335754 | 12/2006 |
| JP | 2010-524538 | 7/2010 |
| JP | 2012051913 | 3/2012 |
| WO | 9927961 | 6/1999 |
| WO | WO 9927961 A1 * 6/1999 | ........... A61K 9/0021 |
| WO | 0126602 | 4/2001 |
| WO | 03026600 | 4/2003 |
| WO | 2006049696 | 6/2006 |
| WO | 2007030477 | 3/2007 |
| WO | WO 2010/022252 | 2/2010 |
| WO | 2010065650 | 6/2010 |

OTHER PUBLICATIONS

Search Report from the GB Intellectual Property Office dated Nov. 16, 2010, for Application No. GB1013405.4, filed Aug. 10. 2010, Applicant, Nemaura Pharma Limited. (2 pages).

* cited by examiner

STRUCTURES FOR TRANSDERMAL DRUG DELIVERY

TECHNICAL FIELD

The invention relates to the field of transdermal delivery of drugs into the body of a patient. In particular, it relates to microstructures of the drug formulation itself that can enhance the process of transporting it through the patient's skin.

For the sake of brevity, the term "drugs" is used in this specification to refer to any biologically active substances that may need to be introduced into the body of a patient to provide a therapeutic or cosmetic effect. The patient may be human or a non-human animal.

BACKGROUND OF THE INVENTION

Methods have been described for enhancing skin permeation of drugs by using a device that gradually eases microneedles into contact with the skin, for example by forming an array of microneedles directly on a roller or, as described in international patent application WO 2008/125798, by forming an array of microneedles on a patch secured to a belt that travels over a set of rollers. This method has been demonstrated to be superior to simply pressing a flat array of microneedles against the skin. That is because less insertion force is required and because, given that the array of needles is inserted row by row, the reproducibility of the dose is also increased independently of the operator.

The main barrier to delivery of drugs through the skin is the stratum corneum, which is a tough outer layer of dead skin cells. The microneedles may be hollow to provide a channel for delivery of a fluid drug through the stratum corneum or they may be solid and simply coated with the drug for delivery. Alternatively, a device comprising solid microneedles may be used to disrupt the stratum corneum and/or to create pores through it in order to enhance its permeability to a drug that is subsequently applied to the surface of the skin, for example in the form of a gel or in a patch.

It has been proposed that the microneedles themselves may be produced from a formulation of the drug. On application to the skin of a patient, the needles break and remain in the skin, where the formulation dissolves and the active substance is absorbed into the blood stream. The formulation may be adapted to give rapid or slow release once the needles have been inserted into the skin. Such needles may be manufactured using metal insert moulds that are laser etched to give high tolerance features and good reproducibility. The mechanical properties of the needles must be such that the needles do not break during their formation, storage or transport, yet they should easily break off upon insertion into the skin. Furthermore the arrays of needles, which usually number hundreds to thousands of individual microneedles, must be mass-produced in a consistent manner for consistent dosing. The micro-manufacture of such moulds for known microneedle arrays is a slow and expensive process. The resulting arrays of microneedles are limited in size.

A further route for delivery of a drug into the body of a patient, especially for treatment of optical disorders, is through the surface of the cornea of the eye. For the purposes of this specification, that route is included within the term "transdermal".

SUMMARY OF THE INVENTION

The invention provides a preparation suitable for transdermal delivery into the body of a patient, the preparation comprising particles of a formulation that is soluble or biodegradable in the body, the particles being rigid, irregular in shape and being angular so that they are capable of penetrating the surface of the skin or of a cornea of the patient. By "irregular", it is meant that the particles are not moulded or otherwise formed to have a consistent shape and size. Because the particles do not need to be precision engineered with a defined height and aspect ratio, this allows them to be manufactured much more simply and cheaply.

By "angular" it is meant that the particles have sharp edges and/or corners that can lodge in pores and crevices in the surface of the skin. When subjected to pressure, the angular particles can be forced into the stratum corneum of the skin (or the surface of the cornea) to be available for deeper absorption into the body. The stratum corneum is several tens of microns thick so it follows that particles containing drug need only breach this barrier of, e.g. 40 microns. According to a preferred definition of "angular", at least 50% of the particles have at least one sharp corner, where a sharp corner is one characterized in that for every pair of faces of the particle that meet at the corner, the angle at which they meet is no greater than 90°. Thus the corner is at least as sharp as the corner of a cube. Another aspect of sharpness of the corners is their radius of curvature. That is preferably much less than the overall size of the particle and in any case no more than a few microns.

The preparation preferably comprises a biologically active substance that has a therapeutic or cosmetic effect. The preparation may comprise a formulation of at least one excipient with the active substance, the excipient being chosen to give the particles the required physical and chemical properties. One suitable excipient is sucrose.

Alternatively, the preparation may be a substance that is biologically inert (but still biocompatible and biodegradable). Its purpose would be to disrupt the stratum corneum of the patient in order to enhance the subsequent transdermal delivery of an active substance into the body of the patient.

The mean size of the particles may be between 10 nm and 1 mm. It is preferably between 1 μm and 100 μm. At the lower end of these ranges, the particles are microstructures much smaller than the types of microneedles that can be manufactured, which aids their absorption by the body. The preferred measure for the size of the particles is their maximum diameter.

The particles may be carried on a transdermal patch for application to the skin of the patient.

Alternatively the particles may be adhered to the tips of one or more projections of a device for assisting delivery of the preparation. The projections of the device preferably have blunt or flat tips. The device may further comprise a container for the preparation and an applicator on which the projections are mounted, the container and the applicator being configured to co-operate so that the projections may be brought into contact with a supply of the preparation stored in the container.

The particles of the preparation can be adhered to the tips of the projections by electrostatic attraction.

The invention further provides a method of manufacturing a preparation for transdermal delivery into the body of a patient, the method comprising the steps of:

preparing a solid aggregate of a formulation that is soluble or biodegradable in the body, the aggregate being cast as a film;

comminuting the solid aggregate to form irregular, angular particles of the formulation.

The preparation step may involve mixing at least one excipient with a biologically active substance.

The comminution step preferably involves grinding the film of solid aggregate. There may be a further step of sieving the particles to adjust the range of particle sizes.

The invention further provides method of delivering a preparation transdermally into the body of a patient, the method comprising the steps of:

applying rigid, irregular, angular particles of the preparation to the surface of the skin or of a cornea of the patient, the preparation being soluble or biodegradable in the body; and applying pressure to the particles to urge them into the skin or cornea.

The step of applying the particles to the skin may comprise applying to the skin a patch carrying the particles.

The step of applying pressure comprises running a roller over the patch or over the surface of the skin to which the particles have been applied. Alternatively, it may comprise pressing one or more blunt-tipped projections against the patch or the surface of the skin. By making use of the sharp edges of the angular particles themselves to penetrate the skin, these methods allow the drug to be spread over a larger area of the skin than could be covered by microneedle arrays.

Alternatively, the step of applying pressure may comprise pressing an array of blunt-tipped microstructures into the surface of the skin, the particles having been previously applied either to the skin or to the microstructures.

DRAWINGS

FIG. 1 schematically shows angular particles according to the invention being applied to the skin of a patient by a patch and pressed into the skin by a roller.

Figure 2:
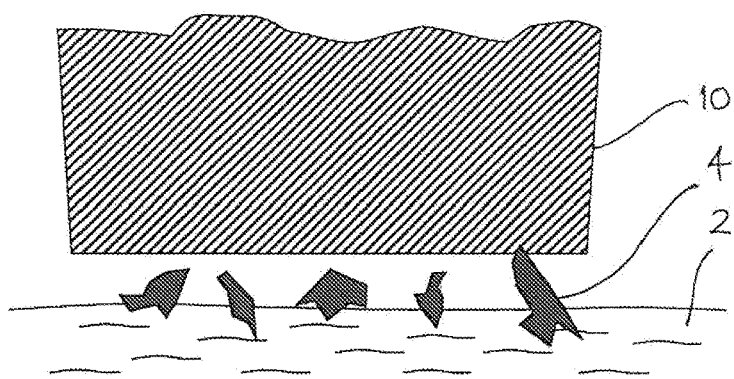

FIG. 2 schematically shows angular particles according to the invention being pressed into the skin of a patient by a projection from a tool.

Figure 3:
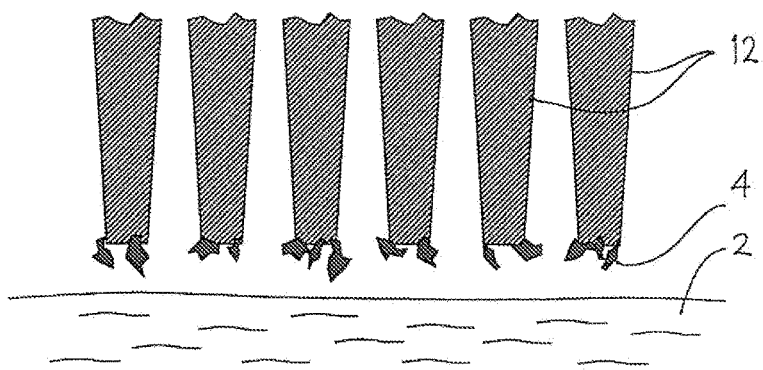

FIG. 3 schematically shows angular particles according to the invention being applied to the skin of a patient on the flat tips of microstructures.

Figure 4:
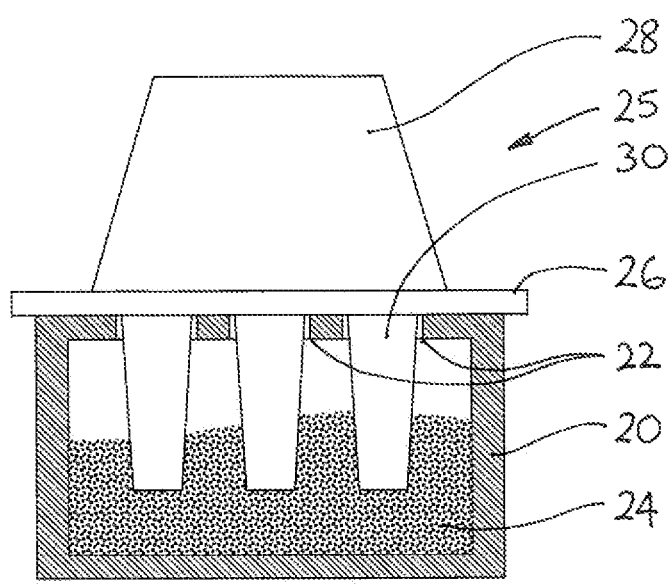

FIG. 4 schematically shows a device for assisting the delivery of particles to the skin of a patient in accordance with the invention.

DETAILED DESCRIPTION OF THE INVENTION

Particles that are sufficiently angular to be pressed through the stratum corneum of a patient's skin may be produced by controlled grinding from an aggregate. The formulations of, typically, an active ingredient combined with one or more excipients and a binder may first be produced as a thin film of aggregate cast onto a substrate then passed through a drying tunnel in a similar manner to a known method of manufacturing membranes. The film can be made as little as a few tens of microns in thickness. The thin film is then gently ground by shearing between two surfaces to cause the aggregate to fracture along natural planes of weakness and produce microstructures (particles) ranging in maximum diameter from nanometers to hundreds of micrometers. A further step of sieving may be used to obtain particles of narrow size ranges.

The process of preparing the particles essentially entails four key steps: production of a wet mix (where the drug is not already available as a solid with the right mechanical properties in its own right), drying the mix, size reduction, and size separation according to the desired particle size range. Drying may be conducted using hot air, dry oven, ambient air drying or vacuum drying, according to the thermal sensitivities of the mix/drug. Milling from a bulk aggregate may be a suitable alternative method of comminuting the formulation to form particles but the aforementioned method of grinding from a thin film has been found more successful at producing the angular particles desired for the present invention.

The preparation may use formulations already reported in scientific and patent literature for the production of microneedles containing an active ingredient. The formulation may comprise a single component, i.e. just the drug itself, if the drug has the right mechanical properties upon being wetted using a suitable solvent, dried and milled to the desired particle size range. In the more common event that the drug alone does not have the right properties when processed in this way, it may be combined with one or more excipient that will impart to it such mechanical properties when processed as described. The key objective is to produce tough, sharp microstructures that will permeate the skin and dissolve on contact with the interstitial fluid.

Excipients that may be used in combination with the drug to impart the desired mechanical and chemical properties would have a number of key functions. One such function is to enhance the binding of the drug particles such that a strong cohesive bond exists that prevents the particles from eroding after their production and on storage, i.e., to reduce the friability of the particles. This class of agents is classified as binding agents. Examples of binding agents include acacia, alginic acid, carboxymethylcellulose, sodium compressible sugar, ethylcellulose gelatin, liquid glucose, methylcellulose, povidone, and pregelatinized starch, amongst others. The amounts of such agents that would be incorporated into a mixture has been well established and documented over several decades of their use primarily in the formulation of tablets.

Another key function of any excipient would be to cause hardening of the particles. Examples of hardening agents include hydrogenated vegetable oils, stearic acid, and silicone. Once again the use of these materials and their compositions is well established in literature, in particular for producing hardened shells and coatings on tablets and caplets, for controlled release and drug taste masking.

A third important class of excipients that may be incorporated into such a system are bulking agents. In some instances the bulking agent would serve multiple functions, and may also impart some binding and hardening properties. These are primarily carbohydrates such as maltose, dextrose, fructose, glucose, trehalose, starch, and cellulose. Biodegradable polymers may also be used, in particular those such as the hydrogels.

Additional excipients may include solvents, lubricants to aid powder flow, viscosity modifying agents, dispersing agents, solubilising agents, polymers to modify drug release and absorption properties, and preservatives.

It has been found experimentally that sucrose is a particularly effective excipient for the formation of suitably shaped particles according to the present invention. The sucrose was mixed with an active ingredient such as ibuprofen or diclofenac, together with sufficient water as a binding agent, and prepared according to the thin film method previously described. With ratios of sucrose:drug greater than 60:40, highly angular particles were produced, and this was especially the case after passing the particles through a 400 µm sieve. The particles remained hard during storage, with little tendency to absorb moisture. It is clearly desirable to use no more excipient than is necessary so a maximum ratio of 20:1 is envisaged.

Molecules that may be suitable for this delivery system essentially include any biologically active agents, including small molecules and proteins and peptides. There is an added advantage of delivering vaccines using this method for two main reasons: firstly the drug is in solid form thus negating thermal stability issues and temperature chain management, and secondly the higher density of Langerhans cells in the skin provide stronger immune responses for a given dose (as recently recorded in literature), allowing smaller doses of vaccines to be administered without affecting therapeutic efficacy. Cosmetic agents such as collagen and agents for removing cellulite would also be suited since such agents do not normally permeate the skin, and this allows not just permeation but also localised drug delivery with the option of modulating the release kinetics through formulation modifications. An important application is in the treatment of pain because of the ability of the invention to deliver analgesics on demand and locally for near instant effect (such as prior to injections or local surgical procedures). Suitable pain-relief drugs would include lidocaine for analgesia and the triptans for migraine. A major problem with burns patients is that the dressings used cause serious levels of irritation thus the ability to delivery active anti-itching agents around the regions where dressings are applied instead of systemic dosing is a clear clinical benefit, and one that will enhance the quality of care.

The particles may be applied to the skin directly using an appropriate implement such as a brush or the particles may be loaded onto a substrate. One such substrate is a standard polymer patch, which provides a convenient medium for transport and storage of a known dose of the preparation prior to applying the patch to the skin for transdermal delivery of the drug. The preparation may be loaded onto the patch by sprinkling or spraying in the desired quantity and configuration, e.g., it may be in arrays, or spread out evenly using a screen to locate the particles on the patch. The particles may be secured to the patch using mechanical or chemical means, e.g., by physically lodging the particles in crevices on the patch, or by adhering to the patch using suitable adhesives respectively. Electrostatic attraction may also be used to apply the particles to a patch. There may be regions across the patch, including the perimeter, with adhesive to secure the patch sufficiently to the skin without any lifting of the patch in the regions where drug absorption is desired after the initial particle insertion.

Whether the particles are applied to the skin directly or via a patch, a hand-held or automated tool may subsequently be used to apply pressure to the treated area and press the particles into the skin. After the application of pressure the patch may be removed or it may be left on the skin for a period. This allows particles remaining on the patch to dissolve gradually in sweat secreted by the skin and their active ingredient to permeate into the skin through the pores previously created in the skin by the jagged particles. The sequence thus provides rapid initial drug entry into the skin, followed by sustained permeation at a lower rate.

The drawings show schematically, and not to scale, various examples of how the application of pressure to the treated area might be achieved, in order to urge the angular particles 4 into the outer layer of skin 2. As shown in FIG. 1, a roller 8 passed over the patch 6 (or alternatively over the surface of the treated skin) is a good way to achieve a uniform pressure over a large area, which is relatively independent of the operator. Alternatively, as shown in FIG. 2, a tool 10 with a flat or convex lower surface may be pressed generally perpendicularly against the treated area of skin 2 (or alternatively against a patch). The pressure may be exerted by hand or by mechanical or pneumatic means. The tool may be driven rapidly towards the skin to increase the force acting on the particles 4. Instead of applying particles first to the skin 2, it would be possible to apply them to the lower surface of the tool 10, which then transfers them to the skin.

If the lower surface of the tool is subdivided so that its area is less than the total footprint of the tool, for example by forming the tool into a number of raised areas or projections, then the force exerted on the tool will be spread over a smaller area and the pressure on those areas will be correspondingly greater.

Taking further this principle of subdividing the active area of the tool leads to an array of high aspect ratio (elongated) projections 12 as shown in FIG. 3. Unlike conventional microneedles, these are formed to have blunt tips so that the projections 12 themselves do not pierce the skin 2 of the patient but merely exert high pressure on the sharp-edged particles 4. The tips are preferably flat, i.e. generally planar and perpendicular to the axis of the microstructures 12 so that they remain parallel to the skin. The microstructures 12 may be produced from any suitable type of plastic, ceramic or metal, and may be from tens of microns to over a millimeter in diameter, with length from tens of microns to several millimeters.

The particles 4 may be attached to the tips of the microstructures 12 by using an adhesive in which the particles are insoluble. They may alternatively be attached through electrostatic attraction to avoid the use of any adhesive that may cause degradation or weakening of the particles during storage. Static charge will be concentrated at the tips of the microstructures and may encourage the particles 4 to align with their longest axes perpendicular to the skin 2, which is likely to be the orientation in which they can penetrate it most easily.

Such projections are preferably arranged on the surface of a roller (not shown) or on a belt passing around a roller (not shown) so that they can move through an arc and be eased one row at a time into contact with the skin as the roller travels across its surface.

FIG. 4 shows a further example of a device that can both store the particulate preparation in accordance with the invention and assist with applying it to the skin of the patient. The lower part of the device comprises a box-shaped container 20 (shown in cross-section) enclosed by a bottom wall, side walls and a top wall. The top wall is pierced by apertures 22, through which the container may be part-filled with the preparation 24 for distribution and storage. The upper part of the device comprises an applicator 25 having a flat base 26, a handle 28 extending upwards from the base, and a set of projections 30 extending downwards from the base.

The projections 30 are elongated and blunt-tipped as described above in relation to FIG. 2. They are arranged so as to align with and extend through the apertures 22 when the base 26 of the applicator 25 rests on top of the container 20. Means (not shown) may be provided for releasably securing the base 25 and the container 20 together to seal the apertures 22 and prevent loss or contamination of the preparation 24 prior to use. As seen in FIG. 4, the tips of the projections 30 dip into the preparation 24 in the container 20 so that they may become coated with particles. By lifting the applicator 25 from the container 20, the projections 30 are withdrawn through the apertures 22 and can then be used to press the particles against the skin of a patient as previously described.

Electrostatic attraction is the preferred way of adhering the particles of the preparation 24 to the projections 30. The preparation 24 may be given an opposite charge to the projections 30 during its manufacture or during filling of the container 20. Alternatively, the applicator may be given an opposite charge to the preparation 24 prior to use. Means such as electrodes (not shown) for generating and/or applying an electric charge may be built into the device. Electrostatic attraction may be sufficient to draw the particles onto the tips of the projections 30 even if the tips do not extend into the reservoir of particles as shown in FIG. 4 but remain poised above them.

The invention claimed is:

1. A device for delivering a preparation into the body of a patient comprising:
   one or more projections, the one or more projections having blunt tips; and
   rigid, irregular in shape, and angular particles adhered to the blunt tips of the one or more projections, the particles being of a formulation that is soluble or biodegradable in the body;
   wherein the device is configured to press the blunt tips of the one or more projections against the surface of at least one of the skin and the cornea of the patient;
   wherein the pressure developed by the blunt tips on the particles against the surface of the at least one of the skin and the cornea results in penetration of the surface of the at least one of the skin and the cornea by the particles; and
   wherein the blunt tips of the one or more projections do not penetrate the surface of the at least one of the skin and the cornea.

2. A device according to claim 1, wherein the projections of the device have flat tips.

3. A device according to claim 1, wherein the projections of the device are an array of elongated microstructures.

4. A device according to claim 1, the device comprising a container for the preparation and an applicator on which the projections are mounted, the container and the applicator being configured to co-operate so that the projections may be brought into contact with a supply of the preparation stored in the container.

5. A device according to claim 1, wherein the particles of the preparation are adhered to the tips of the projections by electrostatic attraction.

6. A device according to claim 5, further comprising means for applying an electrostatic charge to the preparation or to the projections.

* * * * *